United States Patent [19]
Crespi et al.

[11] Patent Number: 5,895,733
[45] Date of Patent: *Apr. 20, 1999

[54] SYNTHESIS METHOD FOR SILVER VANADIUM OXIDE

[75] Inventors: Ann M. Crespi, Minneapolis; Kaimin Chen, New Brighton, both of Minn.

[73] Assignee: Medtronic, Inc., Minneapolis, Minn.

[21] Appl. No.: 08/792,413

[22] Filed: Feb. 3, 1997

[51] Int. Cl.$^6$ .................................................. H01M 4/54
[52] U.S. Cl. ............................................................ 429/219
[58] Field of Search ........................... 429/218, 219; 423/592, 593

[56] References Cited

U.S. PATENT DOCUMENTS

| | | | |
|---|---|---|---|
| 4,016,338 | 4/1977 | Lauck | 429/149 |
| 4,158,722 | 6/1979 | Lauck et al. | 429/194 |
| 4,310,609 | 1/1982 | Liang et al. | 429/194 |
| 4,391,729 | 7/1983 | Liang et al. | 252/182.1 |
| 4,542,083 | 9/1985 | Cava et al. | 429/218 |
| 4,675,260 | 6/1987 | Sakuerai et al. | 429/191 |
| 4,751,157 | 6/1988 | Uchiyama et al. | 429/194 |
| 4,751,158 | 6/1988 | Uchiyama et al. | 429/194 |
| 4,803,137 | 2/1989 | Miyazaki et al. | 429/194 |
| 4,830,940 | 5/1989 | Keister et al. | 429/194 |
| 4,964,877 | 10/1990 | Keister et al. | 29/623.1 |
| 4,965,151 | 10/1990 | Takeda et al. | 429/191 |
| 5,194,342 | 3/1993 | Bito et al. | 429/191 |
| 5,221,453 | 6/1993 | Crespi | 204/291 |
| 5,298,349 | 3/1994 | Takeuchi | 429/219 |
| 5,389,469 | 2/1995 | Passaniti et al. | 429/206 |
| 5,389,472 | 2/1995 | Takeuchi et al. | 429/219 |
| 5,439,760 | 8/1995 | Howard et al. | 429/94 |
| 5,458,997 | 10/1995 | Crespi et al. | 429/219 |
| 5,472,810 | 12/1995 | Takeuchi et al. | 429/218 |
| 5,498,494 | 3/1996 | Takeuchi et al. | 429/219 |
| 5,498,495 | 3/1996 | Takada et al. | 429/219 |
| 5,512,214 | 4/1996 | Koksbang | 252/506 |
| 5,516,340 | 5/1996 | Takeuchi et al. | 29/623.1 |
| 5,545,497 | 8/1996 | Takeuchi et al. | 429/219 |
| 5,558,680 | 9/1996 | Takeuchi et al. | 29/623.1 |
| 5,567,538 | 10/1996 | Oltman et al. | 429/27 |

FOREIGN PATENT DOCUMENTS 63160882  9/1993  Japan.

OTHER PUBLICATIONS

R.A. Leising et al., "Solid–State Cathoe Materials for Lithium Batteries: Effect of Synthesis Temperature on the Physical and Electrochemical Properties of Silver Vanadium Oxide", *Chem. of Materials*, 5, 738–742 (1993). Month N/A H. W. Zandbergen et al., "Two Structures of $Ag_{2-x}V_4O_{11}$, Determined by High Resolution Electron Micropy", *J. of Solid State Chem.*, 110, 167–175 (1994). (Month N/A)

*Primary Examiner*—Maria Nuzzolillo
*Assistant Examiner*—Carol Chaney
*Attorney, Agent, or Firm*—Thomas F. Woods; Harold R. Patton

[57] ABSTRACT

This present invention provides a method for forming C—SVO without the need for flowing $O_2$ during its synthesis. A method of forming silver vanadium oxide in accordance with the present invention includes combining AgO with a vanadium-containing compound to form a mixture; and exposing the mixture to a sufficient temperature for a time effective to form silver vanadium oxide.

20 Claims, 8 Drawing Sheets

5,895,733

SYNTHESIS METHOD FOR SILVER VANADIUM OXIDE

FIELD OF THE INVENTION

The present invention relates to electrochemical cells and cathode material therein, and, in particular, to a synthesis method for silver vanadium oxide cathode material using silver oxide (AgO) as a reactant.

BACKGROUND

A plurality of electrochemical cells are connected together to form a battery. Silver-containing material is widely used as a cathode material in electrochemical cells. Silver-containing cathodes typically contain silver carbonate, silver thiocyanate, divalent silver oxide, silver bismuth oxide, copper silver vanadium oxide, and silver vanadium oxide. Some batteries, when using some of these compounds as the cathode material in individual electrochemical cells therein, however, do not exhibit ideal electrical properties. Ideal electrical properties include a low internal discharge rate (i.e., low increase in internal resistance over lifetime of the cell). A high internal discharge rate undesirably decreases the deliverable capacity (i.e., the integral of current times the discharge time) of a cell. Different cathode materials contribute to different problems. For example, silver chromate undesirably contributes to a large voltage drop during high loads. Divalent silver oxide is soluble and undesirably decomposes over time. These are just a few of the problems associated with some of the above-mentioned cathode materials.

Silver vanadium oxide (SVO) is utilized as a cathode material in lithium (Li) anode electrochemical cells (and, thus, batteries incorporating such electrochemical cells) due to its relatively high volummetric energy density (i.e., the product of capacity times average voltage divided by volume of material), which is particularly desirable for small batteries. The size of the battery is important in implantable medical devices, such as implantable cardiac defibrillators, as illustrated in FIG. 1, so that the device itself occupies a smaller volume within a patients body and is lighter in weight.

SVO is capable of being synthesized using a variety of methods. Methods of synthesis generally fall within two categories, depending on the type of chemical reaction that produces the SVO. SVO can be synthesized using a decomposition reaction, resulting in decomposition-produced SVO (DSVO). Decomposition reactions are known to utilize decomposable metal compounds, such as nitrates, nitrites, carbonates, and ammonium salts for the reacting metal components. A conventional DSVO reaction proceeds from silver nitrate and vanadium pentoxide according to the following reaction: $2\ AgNO_3 + 2\ V_2O_5 \rightarrow Ag_2V_4O_{11} + 2NO_x$. Many conventional DSVO reactions, including the above-mentioned reaction, are not desirable due to the by-products that they produce, such as $NO_x$, which is toxic at certain levels.

Alternatively, SVO can be synthesized using a combination reaction, resulting in combination-produced SVO (C—SVO). C—SVO is characterized by a more crystalline structure, which, when compared to DSVO, contributes to its superior electrical performance in electrochemical cells. Many different silver-containing compounds have been used as reactants in such combination reactions, including $AgVO_3$, $Ag_2O$, and $Ag(0)$. A conventional C—SVO reaction proceeds at a temperature of about 500 degrees Centigrade from silver oxide and vanadium pentoxide according to the following reaction: $Ag_2O + 2\ V_2O_5 \rightarrow Ag_2V_4O_{11}$, as described in U.S. Pat. No. 5,221,453 (Crespi). Crespi also discloses the use of flowing oxygen ($O_2$) gas and Ag(0) according to the following combination reaction: $2\ Ag + 2\ V_2O_5 + 0.5\ O_2 \rightarrow Ag_2V_4O_{11}$. Flowing $O_2$ was used to produce C—SVO having superior electrical performance as compared to CSVO produced in the presence of flowing or stagnant (i.e., having no active gas flow) air. The need for flowing $O_2$, however, requires the use of a sealed retort, a tank of pure oxygen, and a flowmeter, all of which add expense to the synthesis process. Thus, there is a need to reduce the expense associated with the synthesis of SVO, while providing a material that exhibits superior electrical performance when used as a cathode in an electrochemical cell.

Table 1 below lists documents that disclose information of interest to methods of preparation of silver vanadium oxide (SVO) and electrochemical cells containing SVO cathodes, as well as electrochemical cells in general.

TABLE 1

| U.S. Pat. No. | Inventor(s) | Issue Date |
|---|---|---|
| 4,016,338 | Lauck | April 5, 1977 |
| 4,158,722 | Lauck et al. | June 19, 1979 |
| 4,310,609 | Liang et al. | Jan. 12, 1982 |
| 4,391,729 | Liang et al. | July 5, 1983 |
| 4,542,083 | Cava et al. | Sept. 17, 1985 |
| 4,675,260 | Sakurai et al. | June 23, 1987 |
| 4,751,157 | Uchiyama et al. | June 14, 1988 |
| 4,751,158 | Uchiyama et al. | June 14, 1988 |
| 4,803,137 | Miyazaki et al. | Feb. 7, 1989 |
| 4,830,940 | Keister et al. | May 16, 1989 |
| 4,964,877 | Keister et al. | Oct. 23, 1990 |
| 4,965,151 | Takeda et al. | Oct. 23, 1990 |
| 5,194,342 | Bito et al. | March 16, 1993 |
| 5,221,453 | Crespi | June 22, 1993 |
| 5,298,349 | Takeuchi | March 29, 1994 |
| 5,389,472 | Takeuchi et al. | Feb. 14, 1995 |
| 5,439,760 | Howard et al. | Aug. 8, 1995 |
| 5,545,497 | Takeuchi et al. | Aug. 13, 1996 |
| 5,458,997 | Crespi et al. | Oct. 17, 1995 |
| 5,472,810 | Takeuchi et al. | Dec. 5, 1995 |
| 5,498,494 | Takeuchi et al. | March 12, 1996 |
| 5,498,495 | Takeda et al. | March 12, 1996 |
| 5,512,214 | Koksbang | April 30, 1996 |
| 5,516,340 | Takeuchi et al. | May 14, 1996 |
| 5,558,680 | Takeuchi et al. | Sept. 24, 1996 |
| 5,567,538 | Oltman et al. | Oct. 22, 1996 |

Leising et al., Chem. of Materials, 5, 738–42 (1993)

Zandbergen et al., Journal of Solid State Chemistry, 110, 167–175 (1994)

All documents listed in Table 1 above are hereby incorporated by reference herein in their respective entireties. As those of ordinary skill in the art will appreciate readily upon reading the Summary of the Invention, Detailed Description of the Preferred Embodiments, and Claims set forth below, many of the devices and methods disclosed in the documents in Table 1 may be modified advantageously by using the teachings of the present invention.

SUMMARY OF THE INVENTION

The present invention has certain objects. That is, various embodiments of the present invention provide solutions to one or more problems existing in the prior art with respect to implantable medical devices and the batteries used therein. These problems are set forth above. Various embodiments of the present invention have the object of solving at least one of the problems discussed above. Therefore, it is an object of the present invention to provide a method for forming C—SVO material for use in the cathodes of electrochemical cells, particularly for use in implantable medical devices.

To meet one or more of the objects of the invention, the present invention provides a method for forming C—SVO having superior electrical performance without the need for flowing $O_2$ during its synthesis. A method of forming silver vanadium oxide in accordance with the present invention comprises combining AgO with a vanadium-containing compound to form a mixture; and exposing the mixture to a sufficient temperature for a time effective to form silver vanadium oxide. By not requiring flowing $O_2$, the present invention does not require the use of a sealed retort, a tank of pure oxygen, and a flowmeter, all of which add expense to the synthesis process. Thus, the present invention can reduce the expense associated with the synthesis of C—SVO, while providing a material that exhibits superior electrical performance when used as a cathode in an electrochemical cell.

DETAILED DESCRIPTION OF THE PREFERRED EMBODIMENTS

Figure 1:
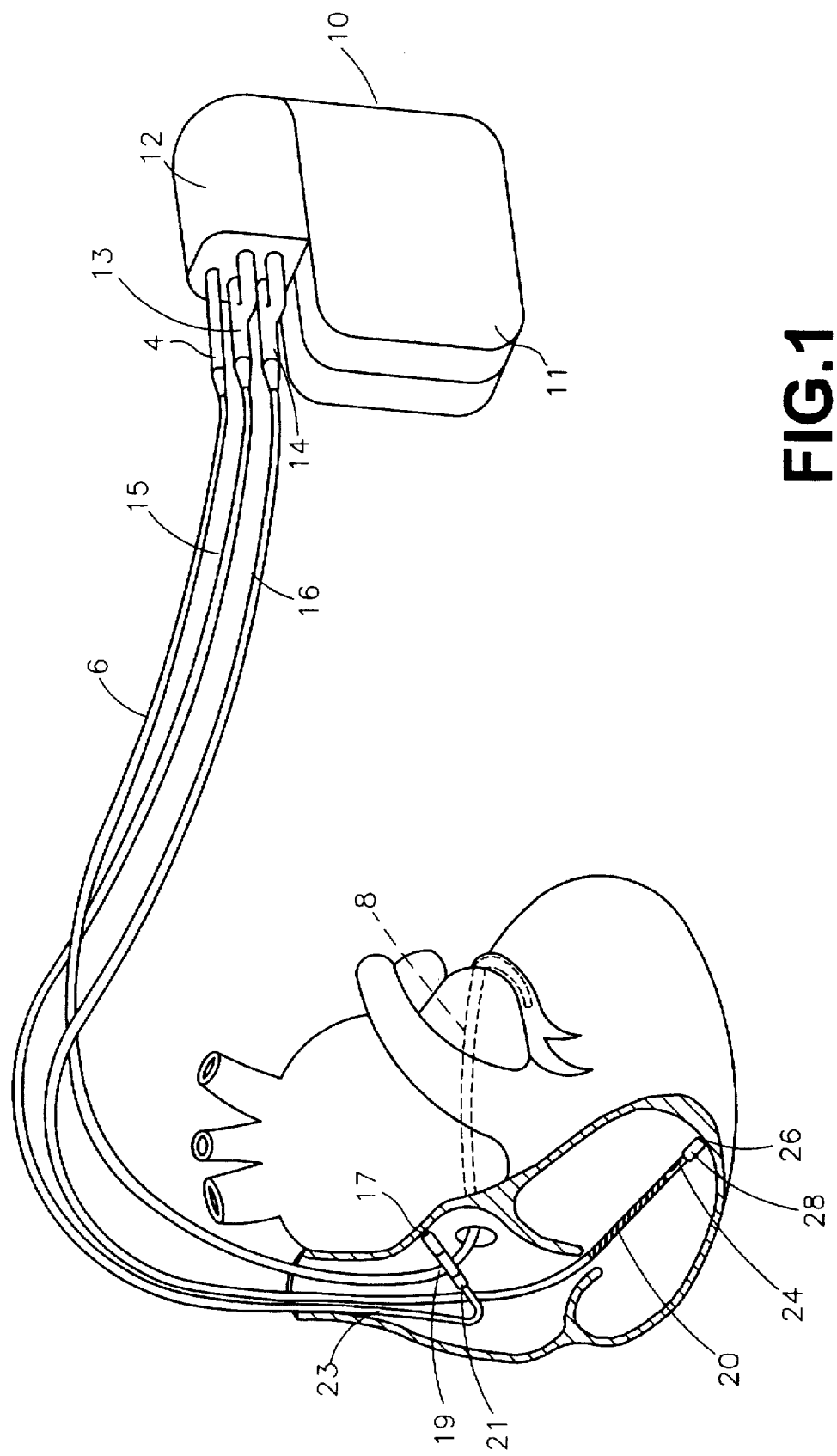
FIG. 1 is a schematic representation of an implantable battery in accordance with the present invention, utilized in an implantable cardiac defibrillator.

The present invention provides a method for synthesizing silver vanadium oxide (SVO) useful as a cathode material in an electrochemical cell. The method of the present invention synthesizes SVO from AgO and a vanadium-containing compound. Preferably, the SVO produced in accordance with the present invention has the formula, $Ag_xV_4O_y$, wherein x is about 1.6 to about 2.2 and y is about 10.5 to about 11.5. More preferably, x is about 2 and y is about 11. Most preferably, the SVO produced has the formula $Ag_2V_4O_{11}$. The resulting SVO is preferably substantially fully oxygenated, which is believed to contribute to superior electrical performance when the SVO is utilized as the cathode material in an electrochemical cell.

According to the present invention, AgO is used instead of $Ag_2O$, for example, which allows for the use of a stagnant atmosphere instead of flowing oxygen gas. This is advantageous because it simplifies the equipment needed for carrying out the synthesis, and also reduces the cost of the synthesis of SVO. The method of the present invention can actually be carried out in a simple box furnace with no atmosphere control.

The reaction between AgO and a vanadium-containing compound can actually produce oxygen as a by-product, which can contribute to producing fully oxygenated SVO. That is, the $O_2$ by-product can help form and maintain a high oxidation state of the SVO, which improves the performance of batteries containing SVO cathodes. The $O_2$ by-product is utilized in the reaction to raise the partial pressure of $O_2$ in the synthesis reaction chamber, allowing for the use of environments that are initially low in $O_2$ content.

Significantly, the AgO can be combined with the vanadium-containing compound in a variety of atmospheres. For example, the reaction can take place in the presence of a gas, such as oxygen ($O_2$), nitrogen ($N_2$), argon (Ar), atmospheric air, or mixtures thereof. The gas can be stagnant or flowing. Preferably, the gas is stagnant, to avoid the need for expensive gas flow equipment. More preferably, the gas is atmospheric air, to avoid the need for expensive $O_2$ flowing equipment. Although it is understood that stagnant air is preferred, thereby allowing for the use of simplified equipment, the method of the present invention is also advantageous because it can produce high quality SVO in a variety of atmospheres.

The vanadium-containing compound can be, for example, $NH_4VO_3$, $VO_2$, $V_2O_3$, $V_2O_5$, $V_2O_4$, $V_3O_7$, $V_4O_9$, $V_6O_{13}$, or mixtures thereof. Preferably, the vanadium-containing compound is one of $V_2O_5$ and $V_6O_{13}$. More preferably, the vanadium-containing compound is $V_2O_5$. When $V_2O_5$ is used as the vanadium-containing compound, the following equation is representative of the reaction: $2\ AgO + 2\ V_2O_5 \rightarrow Ag_2V_4O_{11} + 0.5\ O_2$.

The use of AgO in the method of the present invention allows for the use of compounds in which the vanadium is in a lower oxidation state, as compared to vanadium in $V_2O_5$. The use of lower oxidation state vanadium may result in slightly different crystallographic and electrical properties of the resulting SVO. Thus, $VO_2$, $V_2O_3$, $V_2O_4$, $V_3O_7$, $V_4O_9$, $V_6O_{13}$, or mixtures thereof, can also be used, in which the vanadium exists in a lower oxidation state than in $V_2O_5$. The following equations are representative of methods in which SVO having the formula, $Ag_2V_4O_{11}$, is formed from lower oxidation state vanadium in the presence of $O_2$ gas: $2\ AgO + 4\ VO_2 + \frac{1}{2}\ O_2 \rightarrow Ag_2V_4O_{11}$; $2\ AgO + \frac{2}{3}\ V_6O_{13} + \frac{1}{6}\ O_2 \rightarrow Ag_2V_4O_{11}$; $2\ AgO + V_4O_9 \rightarrow Ag_2V_4O_{11}$; and $AgO + \frac{4}{3}\ V_3O_7 \rightarrow Ag_2V_4O_{11} + \frac{1}{6}\ O_2$. However, variations to the above equations can also yield mixed valence SVO in accordance with the present invention.

According to another aspect of the present invention, a mixture of AgO and $Ag_2O$ can be used to produce SVO. This allows SVO-producing reactions to be tailored to produce desired by-products and use desired reactants. If oxygen flowing equipment is available, for example, the reaction can be tailored to utilize $O_2$ as a reactant. However, it is preferable to be able to synthesis SVO in the presence of stagnant air. Some examples of preferred equations in accordance with this aspect of the invention include: $2\ AgO + Ag_2O + 4V_2O_5 \rightarrow Ag_2V_4O_{11} + \frac{1}{2}\ O_2$ and $2\ AgO + 3\ Ag_2O + 8\ V_2O_5 \rightarrow Ag_2V_4O_{11} + \frac{1}{2}\ O_2$.

According to yet another aspect of the present invention, a mixture of AgO and Ag(0) can be used to produce SVO. Again, this allows SVO-producing reactions to be tailored to produce desired by-products and use desired reactants. Furthermore, a mixture of AgO, Ag(0), and $Ag_2O$ can also be used to produce SVO.

The AgO, and optionally $Ag_2O$ and/or Ag(0), and the vanadium-containing compound(s) are intimately mixed and then exposed to a sufficient temperature for a time effective to produce silver vanadium oxide. Preferably, the reactants are ground together to reduce their particle size and produce a substantially homogeneous mixture. Depending on the desired SVO product, the mixture includes a sufficient molar ratio of silver to vanadium atoms. This molar ratio can vary depending on the vanadium-containing compound and the presence of $Ag_2O$ and/or $Ag(0)$ in addition to the AgO. For example, if $V_2O_5$ is used with AgO, these two reactants are used in approximately equimolar amounts. If, however, $V_4O_9$ is used with AgO, these two reactants are used in a respective equimolar ratio of 1:2 according to the following equation: $2\ AgO+V_4O_9 \rightarrow Ag_2V_4O_{11}$.

The temperature to which this mixture is exposed is about 400° C. to about 600° C. When SVO having the formula $Ag_2V_4O_{11}$ is produced, the temperature is preferably at least about 440 degrees Centigrade, and more preferably at least about 480 degrees Centigrade. It is also preferably no greater than about 550 degrees Centigrade, and more preferably no greater than about 530 degrees Centigrade. Preferably, the mixture is held at the desired temperature for at least about 1 hour, and more preferably for at least about 4 hours. Typically, it can be held at the desired temperature for about 24 hours or longer, although it is preferably held at the desired temperature for no greater than about 8 hours. The time can be extended beyond 24 hours without degrading the resultant SVO, particularly if the reaction is carried out in an $O_2$ atmosphere, although there is typically no advantage to doing so.

After the SVO is synthesized in accordance with reactions of the present invention, the SVO can be ground to provide a smaller particle size. Any conventional method for breaking materials into loose particles can be used to grind the materials. For example, material can be broken into loose particles using a mortar and pestle. There is no need for purification of the material after it is formed.

XRD measurements are one way of characterizing the resulting SVO material. Using Bragg's law, $n\lambda=2d_{hkl}\sin\theta$, the size and shape of a unit cell can be determined from the XRD data. In Bragg's law, the wavelength of an incident beam is represented as $\lambda$ and n is a constant, corresponding to an integral number of $\lambda$s. The angle of incidence of an incident beam on a substrate is represented as $\theta$. The distance between crystallographic planes is represented as $d_{hkl}$. The distance between crystallographic planes, hkl, corresponds to the lattice parameter of a material (i.e., the spacing between adjacent atoms within a crystallographic plane defined by the parameters, hkl). Depending on the crystallographic structure of a material, not every incident beam will be reflected, as neighboring diffracted rays can cancel each other out. The angle of incidence can be varied to determine the distance between crystallographic planes, $d_{hkl}$. Furthermore, by analyzing the intensity of diffracted beams, it can be determined how two or more atoms are distributed at each lattice point.

Figure 2A:
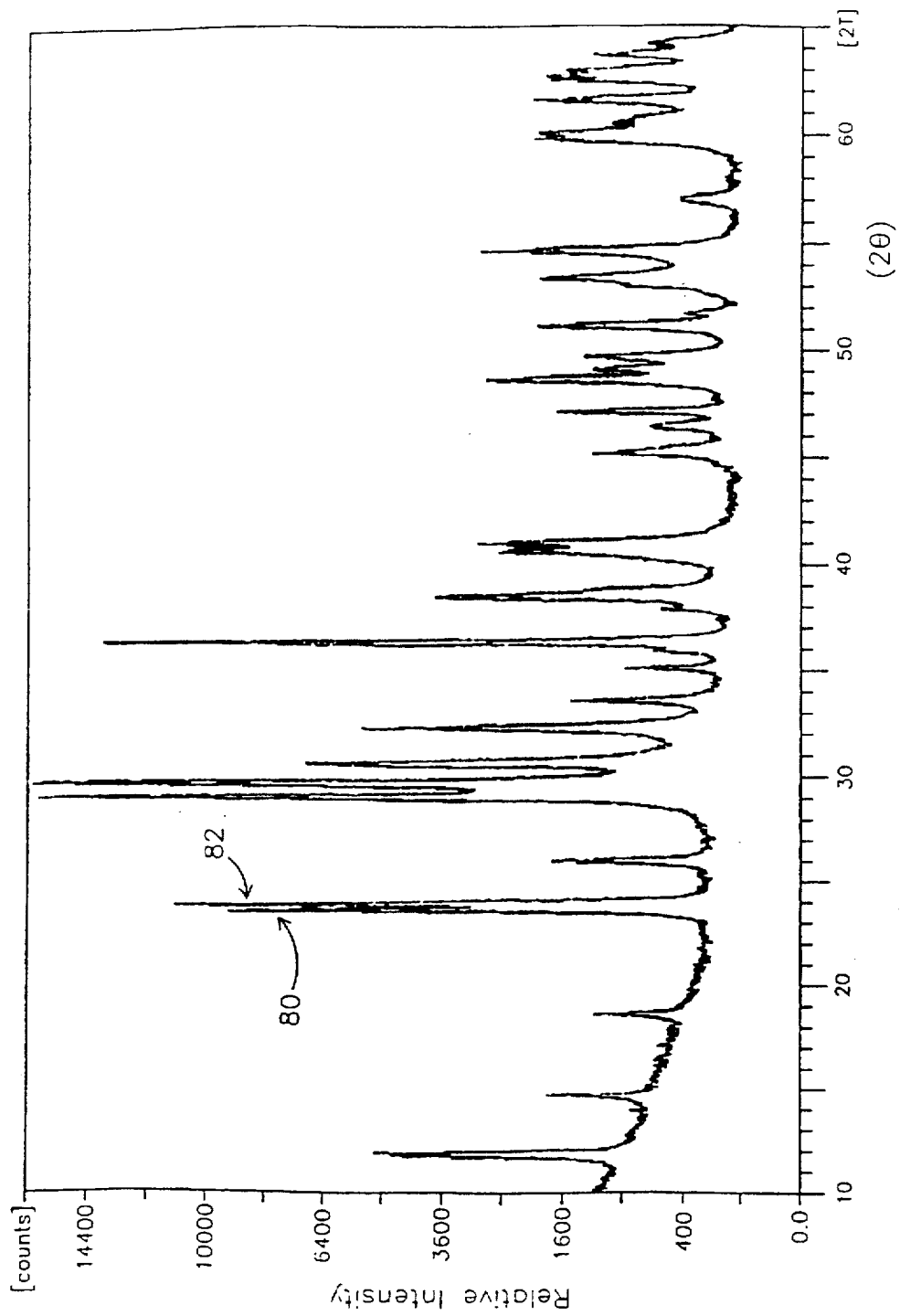
FIG. 2A is a prior art XRD scan (Cu Kα radiation) of C—SVO synthesized using $Ag_2O$ in flowing $O_2$.

For comparison, a prior art C—SVO XRD scan (Cu Kα radiation) is illustrated in FIGS. 2A. C—SVO of FIG. 2A was synthesized in flowing $O_2$ at a temperature of 520° C. for 6 hours, according to the following equation: $Ag_2O+2V_2O_5 V_2O_5 \rightarrow Ag_2V_4O_{11}$. One C—SVO XRD peak 80 is indexed on a C-centered monoclinic cell at about 23.6 degrees (2θ), which corresponds to a {002} crystallographic plane. Another peak 82 is indexed on a C-centered monoclinic cell at about 24.0°(2θ), which corresponds to a {201} crystallographic plane. Because XRD analysis is indicative of the crystal structure of a material, it is desirable to have two resolvable peaks 80 and 82 at about 23° (2θ) to about 25° (2θ) in an SVO XRD scan because this indicates the high degree of crystallinity that is characteristic of conventional C—SVO.

Figure 2B:
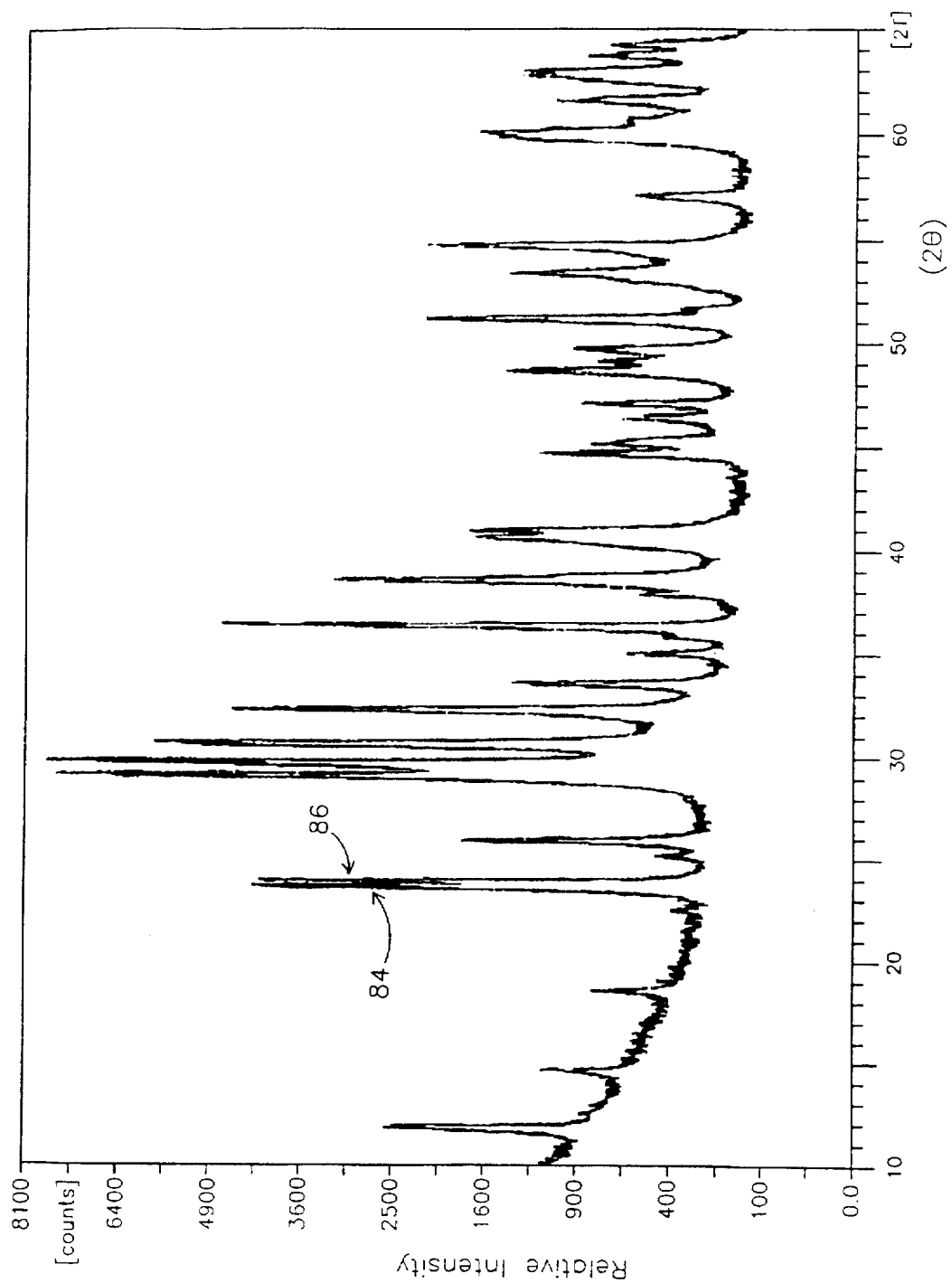
FIG. 2B is an XRD scan (Cu Kα radiation) of C—SVO synthesized using AgO in stagnant air according to the present invention.
Figure 2C:
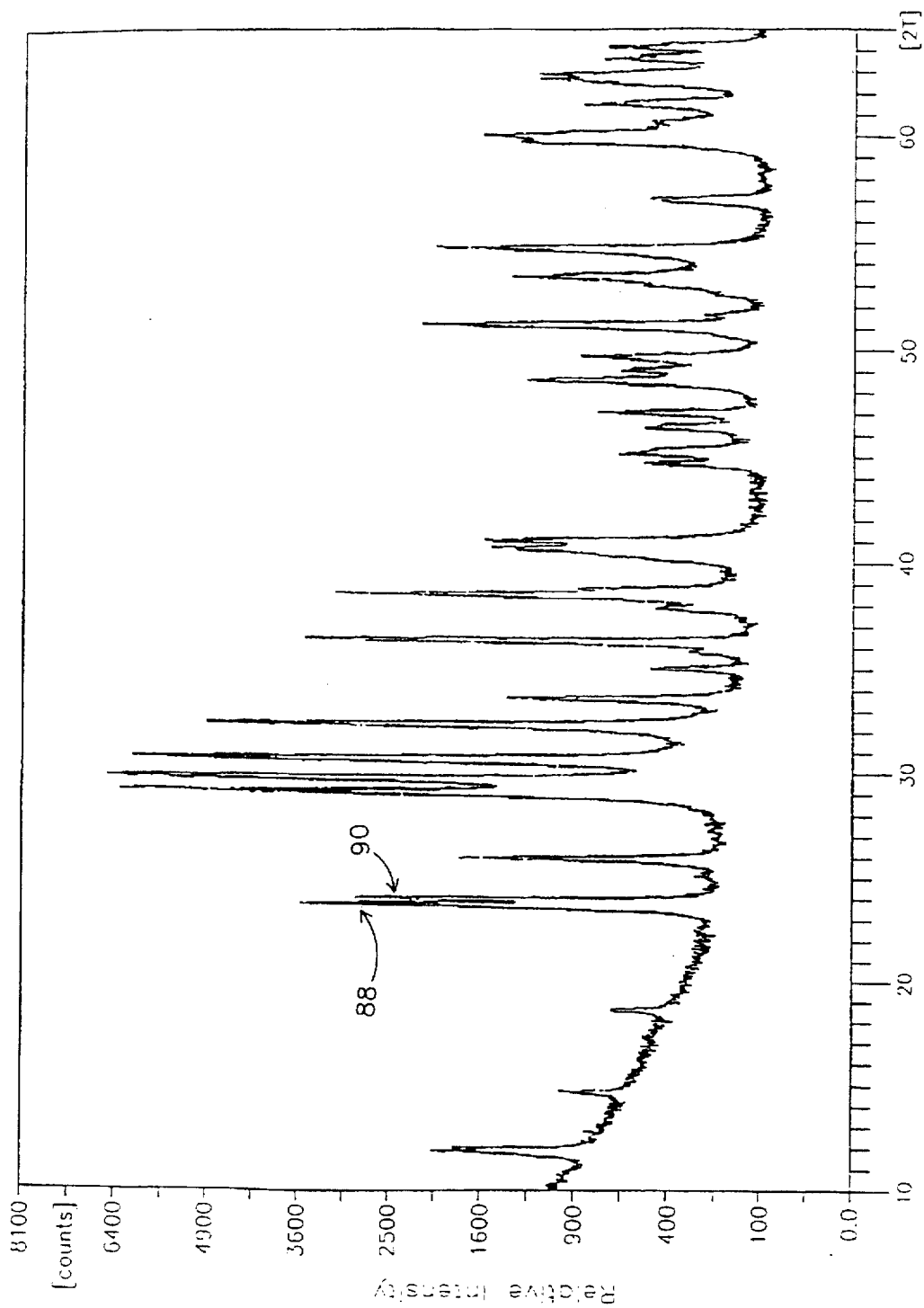
FIG. 2C is an XRD scan (Cu Kα radiation) of CSVO synthesized using AgO in flowing $O_2$ according to the present invention.

FIG. 2B is an XRD scan (Cu Kα radiation) of C—SVO synthesized at a temperature of 520° C. for 6 hours according to the following equation:$2AgO+2\ V_2O_5\ V_2O_5 \rightarrow Ag_2V_4O_{11}+0.5\ O_2$. Stagnant air was used in the processing chamber, without any flowing gases. FIG. 2C is an XRD scan (Cu Kα radiation) of C—SVO synthesized at a temperature of 520° C. for 6 hours according to the following equation: $2\ AgO+2\ V_2O_5\ V_2O_5 \rightarrow Ag_2V_4O_{11}+0.5\ O_2$. Flowing $O_2$ was used in the processing chamber. Both XRD scans (FIGS. 2B and 2C) for C—SVO synthesized in accordance with the present invention are substantially similar to the XRD scan (FIG. 2A) for conventional C—SVO. Thus, the new method of synthesis described herein provides similar resulting C—SVO as CSVO synthesized using $Ag_2O$.

Figure 3:
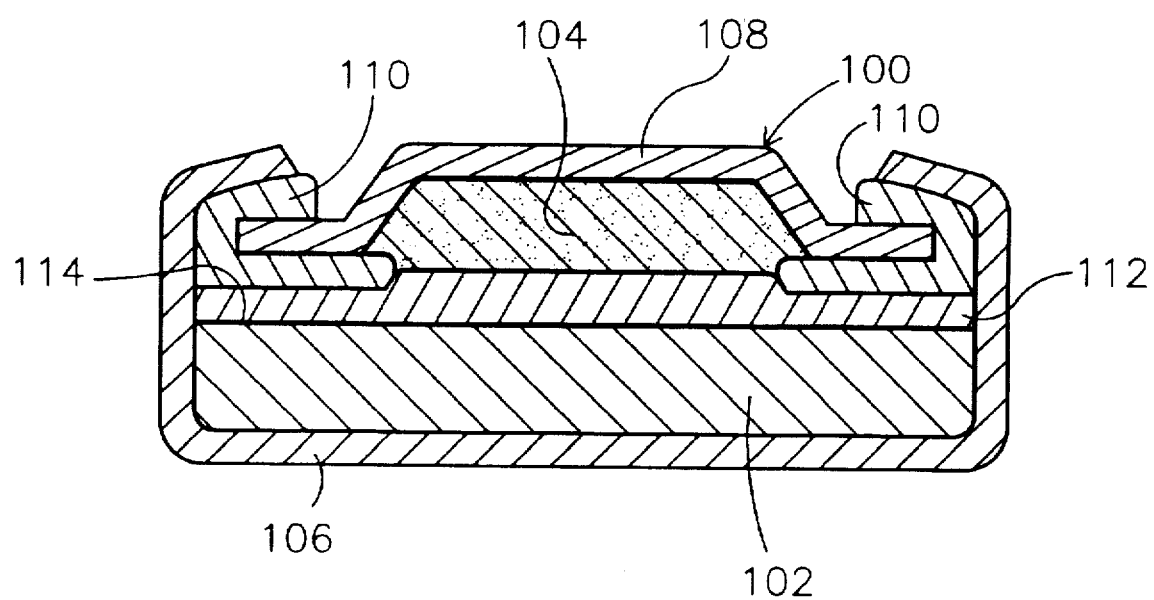
FIG. 3 is a schematic representation of an electrochemical button cell in accordance with the present invention.

SVO made according to the method of the present invention is advantageously used as the cathode material in an electrochemical cell. FIG. 3 illustrates a representative electrochemical button cell. An electrochemical cell 100 comprises a cathode 102 and an anode 104 encased in an anode can 106, which is typically formed of metal, such as titanium or stainless steel. A conventional cap 108 made of nickel/steel/copper alloy, for example, conventional seals 110 made of plastic, for example, and a conventional membrane 112 made of a semi-permeable material, are also typically utilized in the cell 100. An electrolyte 114 separates the anode 104 and the cathode 102. The electrolyte 114 can be an organic or inorganic material, and can be in either the solid or liquid state.

An electrochemical cell 100 operates by developing a differential electrical potential between the cathode 102 and the anode 104. The anode 104 oxidizes to form metal ions during discharge of the cell 100. Li is preferred as the anode 104 material due to its strong electropositivity. Other metals can be used for the anode 104 material, however, including calcium, magnesium, aluminum, and zinc. The cathode 102 converts the metal ions to atomic or molecular forms, thereby conducting an electrical current through the cell 100.

To form the cathode 102 from the SVO, the SVO is pressed into a desired configuration, such as a pressed, cylindrical-shaped pellet, using conventional techniques. For example, the SVO can be dry-pressed or pressed with a small addition of, for example, a liquid electrolyte, a binder (e.g., polytetrafluoroethylene, methyl cellulose, ethyene propylene diene terpolymer (EPDM), polyethylene, polypropylene, polyolefins, fluorinated ethylene propylene (FEP), polyvinylidene fluoride, or mixtures thereof), a conductor (e.g., graphite powder, carbon black, acetylene black powder, or mixtures thereof), and a surfactant. A wide variety of other additives can be added to the SVO prior to pressing it into the desired configuration as well.

A plurality of electrochemical cells can be connected to form an electrode assembly in a battery. The SVO cathode material made according to the method of the present invention can be incorporated into a wide variety of batteries, such as, for example, those shown in U.S. Pat. No. 5,458,997 (Crespi et al.), U.S. Pat. No. 4,830,940 (Keister et al.), U.S. Pat. Nos. 4,964,877 (Keister et al.), and 5,439,760 (Howard et al.).

Figure 4A:
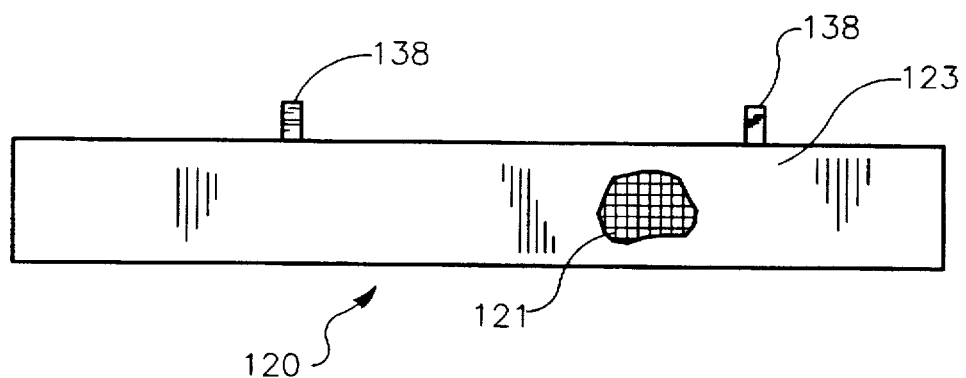
FIG. 4A is a partially cut-away side view of a cathode assembly incorporating CSVO synthesized according to the present invention.
Figure 4B:
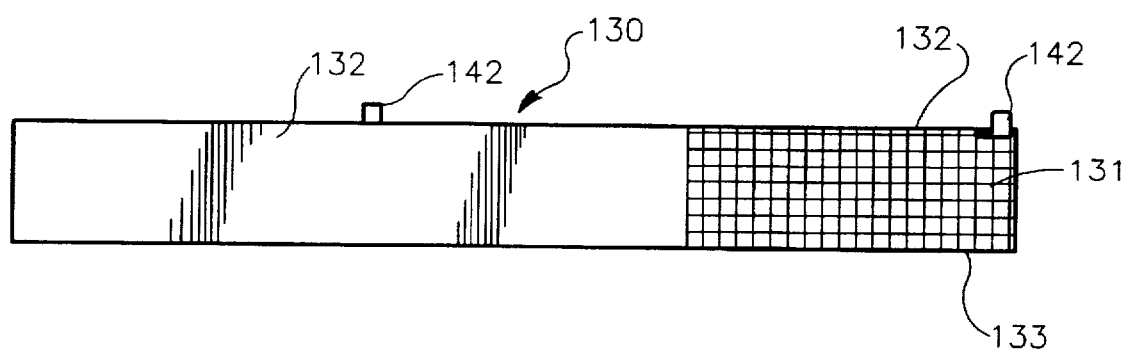
FIG. 4B is a partially cut-away side view of an anode assembly used with the cathode assembly of FIG. 4A.
Figure 4C:
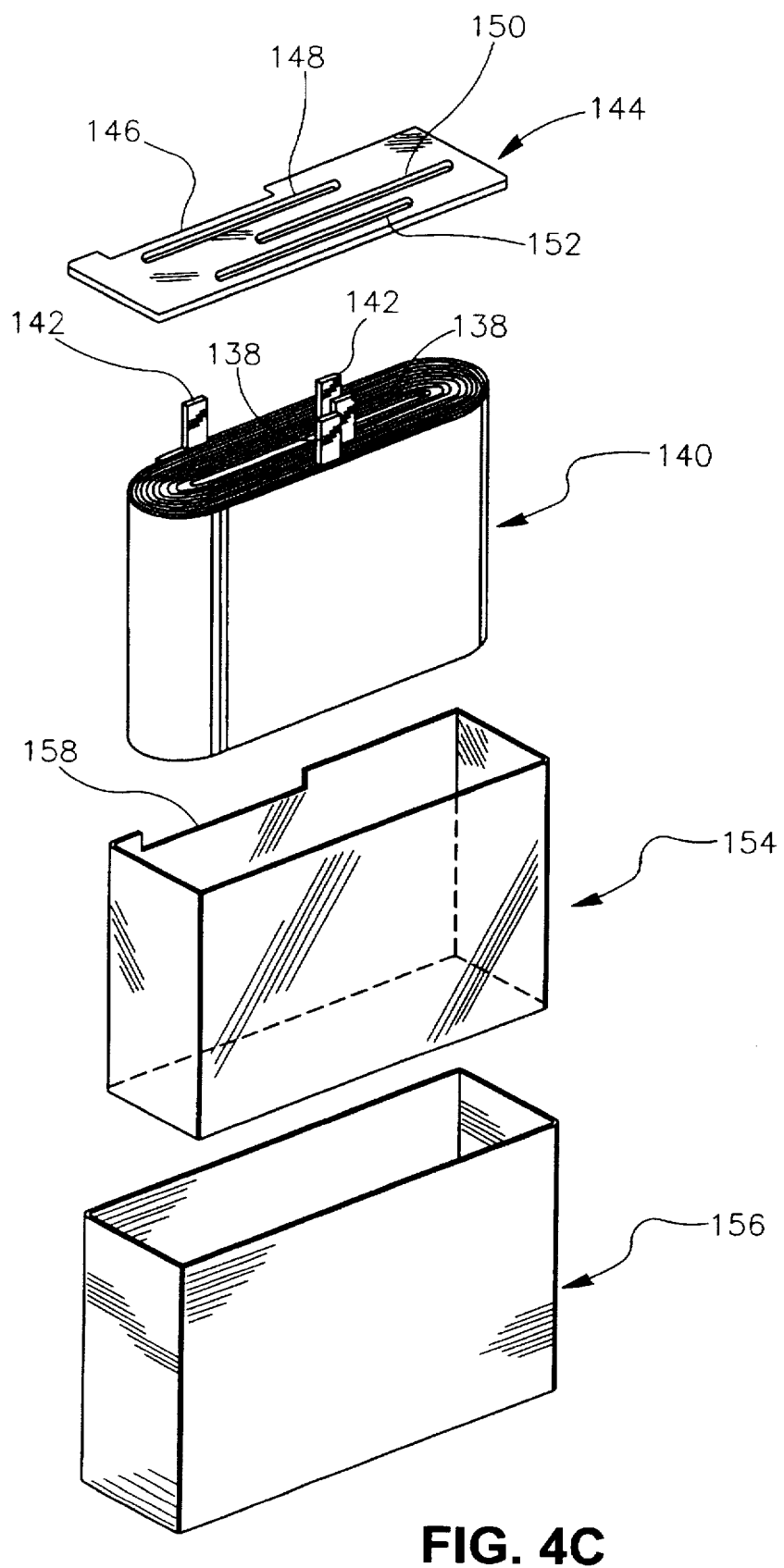
FIG. 4C is a perspective view of a single cell battery incorporating CSVO synthesized according to the present invention.

A specific example of an electrochemical cell in a single-cell battery is shown in FIG. 4C, the cathode and anode of which are shown in FIGS. 4A and 4B, respectively. In this embodiment, a coiled electrode assembly comprised of elongated anode and cathode subassemblies pressed onto a metal current collector and enveloped with a separator of microporous material are overlaid with respect to each other and coiled up. Greater detail of this cell is provided in U.S. Pat. No. 5,439,760 (Howard et al.).

Briefly, with respect to FIG. 4A, which shows an elongated cathode assembly 120, the anode assembly 120 includes a current collector 121 (e.g., titanium, stainless steel, or another conductive metal that is corrosion-resistant when associated with the cathode material), onto which two layers of a cathode material containing heat-treated SVO are pressed. Only one layer of this cathode material (123) is shown in FIG. 4A. The other layer is on the opposite side of the current collector 121. The heat-treated SVO is typically combined with a binder, such as polytetrafluoroethylene, along with carbon black and graphite as conductivity enhancers, dried to a desired moisture content, placed in a uniform layer over the current collector 121, and then dried to form each of the cathode material layers (e.g., 123). Connector tabs 138 project from the edge of the current collector 121.

Briefly, with respect to FIG. 4B, which shows an elongated anode assembly 130, anode assembly 130 includes a screen current collector 131 (e.g., nickel, copper, or another conductive metal that is corrosion-resistant when associated with the alkali metal), which has a first layer of alkali metal 132 on one side and a second layer of alkali metal on the opposite side (not shown). The alkali metal is preferably lithium metal or an alloy of lithium pressed onto the screen current collector 131. In this embodiment, the anode assembly 130 has at one end 133 only alkali metal 132. The bare portion of the current collector 131 will from the outer wrap of the wound electrode assembly as no active material is required for that surface. Connector tabs 142 project from the edge of the current collector 131.

To further complete the assembly of one embodiment of a battery in accordance with the present invention, each of the anode and cathode structures in the electrode assembly 140 is typically encased in a separator material, such as polypropylene or polyethylene, as is further discussed in U.S. Pat. No. 5,439,760 (Howard et al.). A coil insulator 144 is then placed over the electrode assembly 140. The coil insulator 144 includes a notch 146 and a slit 148 to accommodate anode lead portions 142. The coil insulator 144 further includes slits 150 and 152 to accommodate cathode lead portions 138. The electrode assembly 140 is inserted in an insulative case liner 154, which is then inserted in a case 156. The insulative case liner 154 preferably extends at its top edge above the edge of the electrode assembly 131 in order to provide an overlap with other insulative elements. It may also include a notch 158 on one side in order to allow easy connection of the anode lead portions 142 to the case 156. The coil insulator 144 and case liner 154 are preferably made from a polyolefin polymer or a fluoropolymer, such as ethylene tetrafluoroethylene copolymer (ETFE). The case 156 is preferably made of stainless steel or titanium. It is to be understood that many other battery configurations can be formed with the improved cathode material in accordance with the present invention.

Electrochemical cells according to the present invention can be used in batteries such as those utilized in implantable cardiac defibrillators 160, as illustrated in FIG. 1.

FIG. 1 illustrates a defibrillator and lead set according to the present invention. The ventricular lead includes an elongated insulative lead body 16, carrying three concentric coiled conductors, separated from one another by tubular insulative sheaths. Located adjacent the distal end of the lead are a ring electrode 24, an extendible helix electrode 26 mounted retractably within an insulative electrode head 28, and an elongated coil electrode 20. Each of the electrodes is coupled to one of the coiled conductors within lead body 16. Electrodes 24 and 26 are employed for cardiac pacing and for sensing ventricular depolarizations. At the proximal end of the lead is a bifurcated connector 14 which carries three electrical connectors, each coupled to one of the coiled conductors. The defibrillation electrode 20 may be fabricated from platinum, platinum alloy or other materials known to be usable in implantable defibrillation electrodes and may be about 5 cm in length.

The atrial/SVC lead includes an elongated insulative lead body 15, carrying three concentric coiled conductors, separated from one another by tubular insulative sheaths, corresponding to the structure of the ventricular lead. Located adjacent the J-shaped distal end of the lead are a ring electrode 21 and an extendible helix electrode 17, mounted retractably within an insulative electrode head 19. Each of the electrodes is coupled to one of the coiled conductors within the lead body 15. Electrodes 17 and 21 are employed for atrial pacing and for sensing atrial depolarizations. An elongated coil electrode 23 is provided, proximal to electrode 21 and coupled to the third conductor within the lead body 15. Electrode 23 preferably is 10 cm in length or greater and is configured to extend from the SVC toward the tricuspid valve. In one preferred embodiment tested by the inventors, approximately 5 cm of the right atrium/SVC electrode was located in the right atrium, with the remaining 5 cm located in the SVC. At the proximal end of the lead is a bifurcated connector 13 which carries three electrical connectors, each coupled to one of the coiled conductors.

The coronary sinus lead includes an elongated insulative lead body 6, carrying one coiled conductor, coupled to an elongated coiled defibrillation electrode 8. Electrode 8, illustrated in broken outline, is located within the coronary sinus and great vein of the heart. At the proximal end of the lead is a connector plug 4 which carries an electrical connector, coupled to the coiled conductor. The coronary sinus/great vein electrode 8 may be about 5 cm in length.

An implantable pacemaker/cardioverter/defibrillator 10 is shown in combination with the leads, with the lead connector assemblies 4, 13 and 14 inserted into the connector block 12. Optionally, insulation of the outward facing portion of the housing 11 of the pacemaker/cardioverter/defibrillator 10 may be provided using a plastic coating, for example parylene or silicone rubber, as is currently employed in some unipolar cardiac pacemakers. However, the outward facing portion may instead be left uninsulated, or some other division between insulated and uninsulated portions may be employed. The uninsulated portion of the housing 11 optionally serves as a subcutaneous defibrillation electrode, used to defibrillate either the atria or ventricles. Other lead configurations and electrode locations may of course be substituted for the lead set illustrated. For example, atrial defibrillation and sensing electrodes might be added to either the coronary sinus lead or the right ventricular lead instead of being located on a separate atrial lead, thereby allowing for a two-lead system.

Specific methods and apparatus embodying the invention are described in the following examples. These examples are merely illustrative of the many possible embodiments of the invention.

EXAMPLES

Example 1

Preparation of C—SVO

An equimolar mixture of AgO (4.5 g) and $V_2O_5$ (6.6 g) was ground with a mortar and pestle to produce a homogenous mixture. The mixture was placed in an alumina crucible, which was then placed in a Lindberg furnace under air at atmospheric pressure. The reaction was then carried out at 520° C. and a heating rate of 5° C./minute for 6 hours.

Example 2

Preparation of C—SVO

A mixture of AgO (3.0 g) and $V_6O_{13}$ (4.15 g) was ground with a mortar and pestle to produce a homogenous mixture. The mixture was placed in an alumina crucible, which was then placed in a Lindberg furnace under $O_2$ flow at a flow rate of 100 mL/minute. The reaction was then carried out at 520° C. and a heating rate of 5° C./minute for 6 hours.

Example 3

Preparation of C—SVO

A mixture of AgO (1.0 g), $Ag_2O$ (0.935 g), and $V_2O_5$ (2.939 g) was ground with a mortar and pestle to produce a homogenous mixture. The mixture was placed in an alumina crucible, which was then placed in a Lindberg furnace under air at atmospheric pressure. The reaction was then carried out at 500° C. and a heating rate of 5° C./minute for 6 hours.

Example 4

Formation of C—SVO Cathode

SVO of the invention was mixed with a polymeric binder (polytetrafluoroethylene), graphite powder, and carbon black. The mixture contained 91% SVO, 5% polymeric binder (polytetrafluoroethylene), 2% carbon black, and 2% graphite powder. The method of Howard et al., supra, (U.S. Pat. No. 5,439,760) was employed thereafter to prepare the SVO and cathode of the present invention. A disc-shaped pellet having an area on one major surface thereof of about 2.8 centimeters squared was cut from the resulting sheet of cathode material to form a cathode for use in an electrochemical cell.

Example 5

Formation of an Electrochemical Cell

A pressed pellet was formed to utilize as the cathode in an electrochemical cell. The SVO utilized in the cathode was prepared according to Example 1. The cathode contained a titanium current collector and consisted of 91% active cathode material, 5% polymer binder (polytetrafluoroethylene), 2% carbon black, and 2% graphite powder. The cathode was assembled with a lithium anode and an electrolyte consisting of 1.0M $LiAsF_6$ in 50% by volume propylene carbonate and 50% by volume dimethoxyethane.

Example 6

Testing of Electrochemical Cells

Figure 5:
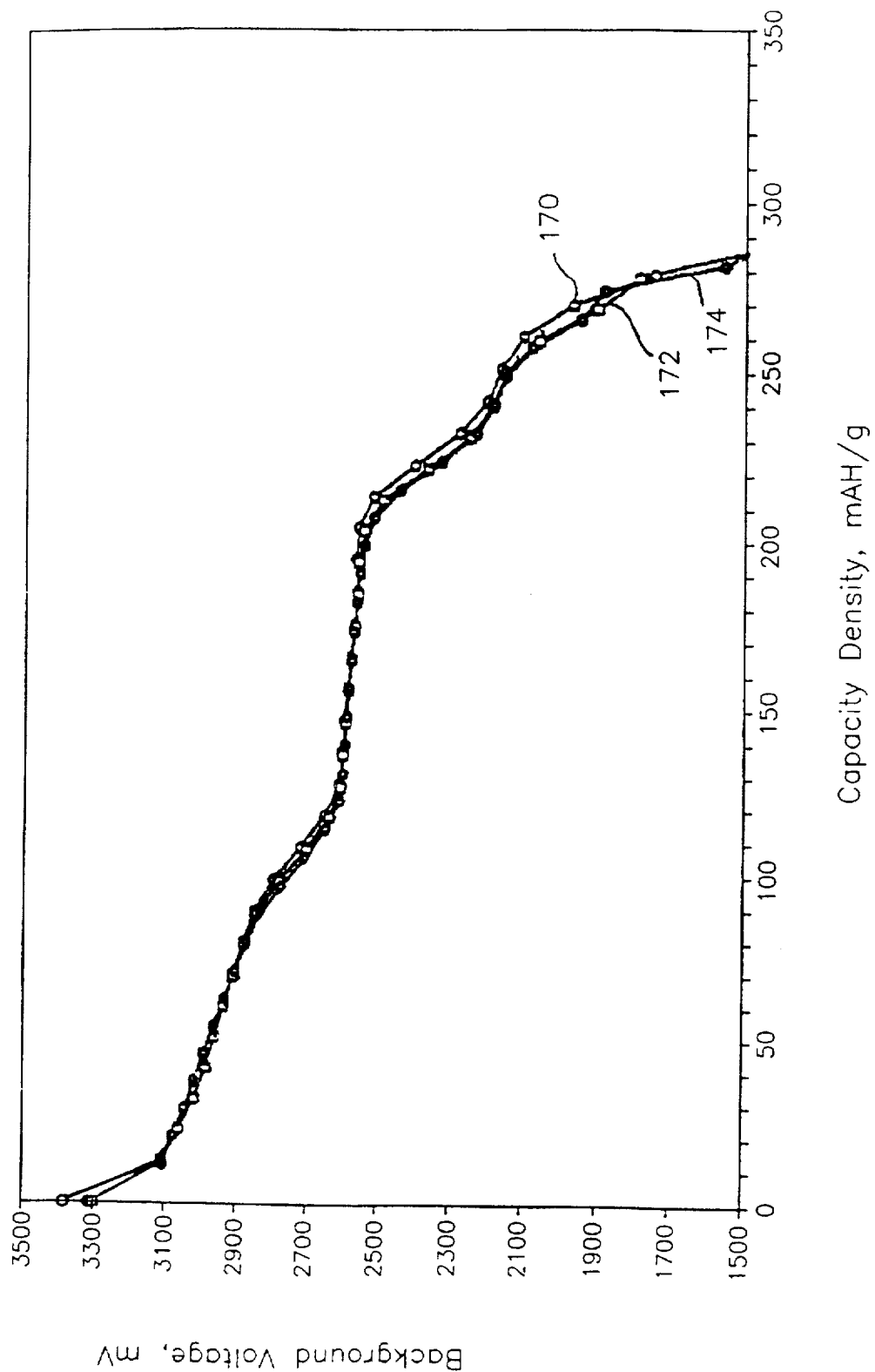
FIG. 5 is a graphical representation of background voltage versus capacity density for discharge curves of electrochemical cells utilizing cathode material made according to the present invention and tested at 37° C. and a 28 kΩ load.

A discharge test was conducted for an electrochemical cell made in accordance with Example 5, as shown by curve 170 in FIG. 5. A second electrochemical cell was made in accordance with Example 5, but, however, SVO was synthesized in the presence of flowing $O_2$ instead of atmospheric air. The discharge test for this second electrochemical cell is shown by curve 172 in FIG. 5. A third electrochemical cell was made in accordance with Example 5, but, however, a different SVO cathode material was utilized. The SVO cathode material utilized for this third electrochemical cell was synthesized at 520° C. for 6 hours in flowing $O_2$ according to the prior art equation: $Ag_2O + 2V_2O_5\ V_2O_5 \rightarrow Ag_2V_4O_{11}$. The discharge test for this third electrochemical cell is shown by curve 174 in FIG. 5.

The cathode of all three cells contained a titanium current collector and consisted of 91% active cathodes material, 5% polymer binder (polytetrafluoroethylene), 2% carbon black, and 2% graphite powder. The electrolyte was 1.0M $LiAsF_6$ in 50% by volume propylene carbonate an 50% by volume dimethoxyethane.

The electrochemical cells were discharged at an operating temperature of 37 degrees C. with a resistive load of 28 kohms.

Comparative results are illustrated in FIG. 5. FIG. 5 illustrates the background voltage versus delivered capacity for the three electrochemical cells. The similarity of the three discharge curves 170, 172, and 174 indicates that all three electrochemical cells have similar capacity densities. Thus, SVO prepared in accordance with the present invention can be effectively utilized in electrochemical cells, producing equivalent electrical discharge characteristics as C—SVO prepared according to conventional methods.

Example 7

X-Ray Diffraction Analysis

A Philips XPert diffractometer (Philips Electronics, Mahwa, N. J.) was used for the measurements. The data collection time used was 8 seconds per step and a step size of 0.02° (2θ). Philips PC-APD 4.0b software was used to analyze the XRD data collected. For the XRD scans presented herein, an incident beam was deflected off a copper target having a wavelength of 1.5406 angstroms to produce Cu Kα radiation. The angle of incidence was varied to determine the distance between crystallographic planes, $d_{hkl}$.

For comparison, a prior art C—SVO XRD scan (Cu Kα radiation ) is illustrated in FIGS. 2A. CSVO of FIG. 2A was synthesized in flowing $O_2$ at a temperature of 520° C. for 6 hours, according to the following equation: $Ag_2O + 2V_2O_5\ V_2O_5 \rightarrow Ag_2V_4O_{11}$. One C—SVO XRD peak 80 was indexed on a C-centered monoclinic cell at about 23.6 degrees (2θ), which corresponds to a {002} crystallographic plane. Another peak 82 was indexed on a C-centered monoclinic cell at about 24.0° (2θ), which corresponds to a {201} crystallographic plane. Because XRD analysis is indicative of the crystal structure of a material, it is desirable to have two resolvable peaks 80, 82 at about 23° (2θ) to about 25° (2θ) in an SVO XRD scan because this indicates the high degree of crystallinity that is characteristic of conventional CSVO.

FIG. 2B is an XRD scan (Cu Kα radiation ) of C—SVO synthesized at a temperature of 520° C. for 6 hours according to the following equation: $2\ AgO + 2\ V_2O_5\ V_2O_5 \rightarrow Ag_2V_4O_{11} + 0.5\ O_2$. Stagnant air was used in the processing chamber, without any flowing gases. FIG. 2C is an XRD scan (Cu Kα radiation ) of C—SVO synthesized at a temperature of 520° C. for 6 hours according to the following equation: $2\ AgO + 2\ V_2O_5\ V_2O_5 \rightarrow Ag_2V_4O_{11} + 0.5\ O_2$. Flowing $O_2$ was used in the processing chamber. Both XRD scans (FIGS. 2B and 2C) for C—SVO synthesized in accordance with the present invention are substantially similar to the XRD scan (FIG. 2A) for conventional CSVO. Thus, XRD analysis further indicates that the new method of synthesis described herein provides similar resulting CSVO as CSVO synthesized using $Ag_2O$.

All patents, patent applications, and publications disclosed herein are incorporated by reference in their entirety, as if individually incorporated. The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to a method for forming a cathode material for use in implantable medical devices. The present invention is also not limited to a method for forming a cathode material for use in an electrochemical cell per se, but may find further application as a method for forming a ceramic material. That is, the present invention includes within its scope, methods of making various silver vanadium oxide compounds described hereinabove.

What is claimed is:

1. A method of forming an electrochemical cell, comprising:

combining AgO with a vanadium oxide compound to form a mixture;

exposing the mixture to a sufficient temperature for a time effective to form silver vanadium oxide;

forming a cathode comprising the silver vanadium oxide;

providing an anode;

providing an electrolyte; and assembling the cathode, the anode, and the electrolyte into the electrochemical cell.

2. The method of claim 1 wherein the silver vanadium oxide has the formula $Ag_xV_4O_y$, wherein x is about 1.6 to about 2.2 and y is about 10.5 to about 11.5.

3. The method of claim 2 wherein y is about 11.

4. The method of claim 2 wherein x is about 2.

5. The method of claim 1 wherein the exposing step further comprises simultaneously supplying a gas in a reaction chamber with the AgO and the $V_2O_5$, wherein the gas is selected from the group of oxygen, nitrogen, argon, atmospheric air, and mixtures thereof.

6. The method of claim 5 wherein the step of supplying a gas comprises supplying stagnant atmospheric air.

7. The method of claim 1 wherein the step of exposing comprises exposing the mixture to a temperature of about 440 degrees C. to about 550 degrees C. for at about 1 hour to form silver vanadium oxide.

8. The method of claim 7 wherein the step of exposing comprises exposing the mixture to a temperature of about 440 degrees C. to about 550 degrees C. for about 4 hours to about 8 hours to form silver vanadium oxide.

9. A method of making a sealed electrochemical cell for an implantable medical device, the cell comprising a lithium anode in electrical contact with an anode can within which the cell components are housed, a silver vanadium oxide cathode, an electrolyte and a separator disposed between the anode and the cathode, comprising the steps of:

(a) combining divalent silver oxide with a vanadium-containing compound to form a mixture;

(b) exposing the mixture to a sufficient temperature for a time effective to form a silver vanadium oxide material;

(c) combining the silver vanadium oxide material with a binder and a conductivity enhancer to form a cathode material;

(d) forming the cathode from the cathode material; and (e) placing the cathode, the anode and the separator in the can.

10. The method of claim 9, further comprising the step of sealing the can to form the cell after the anode, the cathode and the separator have been disposed therewithin.

11. The method of claim 9, wherein the electrolyte is introduced in the can after the anode, the cathode and the separator have been disposed therewithin.

12. The method of claim 9, wherein the cathode material combination step includes the step of adding an electrolyte to the cathode material.

13. The method of claim 9, wherein the cathode material combination step includes the step of adding a surfactant to the cathode material.

14. The method of claim 9, wherein the cathode forming step includes the step of pressing the cathode material into a cylindrically-shaped pellet for use in a button cell.

15. The method of claim 9, wherein the cathode forming step includes the step of pressing the cathode material into a strip-shaped configuration for use in a spirally-wound cell.

16. The method of claim 9, wherein the can is formed of a material selected from the group consisting of titanium and stainless steel.

17. The method of claim 9, wherein the electrolyte is selected from the group consisting of a liquid electrolyte, a solid electrolyte, an organic electrolyte and an inorganic electrolyte.

18. The method of claim 9, wherein the binder is material selected from the group consisting of polytetrafluoroethylene, methyl cellulose, ethylene propylene diene terpolymer (EPDM), polyethylene, polypropylene, polyolefins, fluorinated ethylene propylene (FEP), polyvinylidene fluoride, and combinations or mixtures thereof.

19. The method of claim 9, wherein the conductivity enhancer is selected from the group consisting of graphite powder, carbon black, acetylene black powder, and combinations or mixtures thereof.

20. The method of claim 9, wherein the implantable medical device is a defibrillator.

* * * * *